US012691285B2

(12) United States Patent
Bakx

(10) Patent No.: US 12,691,285 B2
(45) Date of Patent: Jul. 28, 2026

(54) MEDICAL DEVICES, SYSTEMS, AND METHODS THAT ADJUST PHYSIOLOGICAL SIGNAL THRESHOLDS TO CONTROL STIMULATION THERAPY

(71) Applicant: MEDTRONIC, INC., Minneapolis, MN (US)

(72) Inventor: Martinus Adrianus Godefridus Maria Bakx, Geleen (NL)

(73) Assignee: Medtronic, Inc., Minneapolis, MN (US)

( * ) Notice: Subject to any disclaimer, the term of this patent is extended or adjusted under 35 U.S.C. 154(b) by 294 days.

(21) Appl. No.: 18/225,675

(22) Filed: Jul. 24, 2023

(65) Prior Publication Data

US 2024/0033520 A1     Feb. 1, 2024

Related U.S. Application Data

(60) Provisional application No. 63/393,848, filed on Jul. 30, 2022.

(51) Int. Cl.
A61N 1/36 (2006.01)

(52) U.S. Cl.
CPC ..... A61N 1/36139 (2013.01); A61N 1/36192 (2013.01)

(58) Field of Classification Search
CPC ...................................... A61N 1/36135–36139
See application file for complete search history.

(56) References Cited

U.S. PATENT DOCUMENTS

| | | | | |
|---|---|---|---|---|
| 5,074,302 | A | * | 12/1991 | Poore ................. A61N 1/36542 |
| | | | | 607/19 |
| 7,783,353 | B2 | * | 8/2010 | Libbus ............... A61N 1/36564 |
| | | | | 607/18 |
| 8,521,294 | B2 | | 8/2013 | Sarma et al. |
| 8,620,425 | B2 | * | 12/2013 | Zhou ................. A61N 1/36114 |
| | | | | 607/9 |
| 9,089,267 | B2 | * | 7/2015 | Hincapie Ordonez ...................... |
| | | | | A61N 1/36139 |
| 10,390,766 | B2 | | 8/2019 | Fiveland et al. |
| 10,589,096 | B2 | | 3/2020 | Tandon |
| 10,625,082 | B2 | | 4/2020 | Laghi |
| 10,688,306 | B2 | | 6/2020 | Strother et al. |
| 10,987,016 | B2 | | 4/2021 | Laughlin et al. |
| 11,033,732 | B2 | | 6/2021 | Cheeran et al. |
| 11,129,991 | B2 | * | 9/2021 | Dinsmoor ............ A61N 1/3606 |
| 2007/0142864 | A1 | * | 6/2007 | Libbus ............... A61N 1/36542 |
| | | | | 607/2 |
| 2014/0350634 | A1 | | 11/2014 | Grill et al. |
| 2019/0388695 | A1 | * | 12/2019 | Dinsmoor ............ A61N 1/3606 |

(Continued)

*Primary Examiner* — Eric D. Bertram
(74) *Attorney, Agent, or Firm* — Shumaker & Sieffert, P.A.

(57) ABSTRACT

Medical devices that provide stimulation therapy that is adjusted based on sensed physiological signals compensate for drifting of those physiological signal values that can lead to stimulation control reaching limits and becoming less effective. The medical devices determine average values of the physiological signals and use those average values to compute adjusted physiological signal threshold(s). The adjusted threshold(s) bring the physiological signals closer to or within the threshold(s) to allow the stimulation adjustments to be made within stimulation limits that can influence the physiological signal to continue to be within the threshold(s) and provide more effective therapy.

20 Claims, 6 Drawing Sheets

(56)                    References Cited

U.S. PATENT DOCUMENTS

| | | |
|---|---|---|
| 2021/0106830 A1 | 4/2021 | Provenza et al. |
| 2021/0290946 A1 | 9/2021 | Laughlin et al. |
| 2021/0346699 A1 | 11/2021 | Miocinovic et al. |
| 2022/0016415 A1 | 1/2022 | Arlotti et al. |
| 2022/0257950 A1 | 8/2022 | Moore et al. |

* cited by examiner

MEDICAL DEVICES, SYSTEMS, AND METHODS THAT ADJUST PHYSIOLOGICAL SIGNAL THRESHOLDS TO CONTROL STIMULATION THERAPY

RELATED APPLICATIONS

The present application claims priority to U.S. Prov. Appl. No. 63/393,848, filed om Jul. 30, 2022.

TECHNICAL FIELD

Embodiments relate to medical devices, systems, and methods that provide stimulation therapy, and embodiments more particularly relate to the adjustment of physiological signal thresholds used by the devices, systems, and methods to control the stimulation therapy being provided.

BACKGROUND

Patients suffering from certain medical conditions may benefit from electrical stimulation therapy. A medical system, such as an external or implantable stimulator coupled to an implantable lead, provides this electrical stimulation therapy to a target site within the body of the patient. For instance, certain neurological conditions may benefit from the stimulation therapy being provided to neural tissue in the brain, the spine, or elsewhere in the body. The implantable medical lead extending from the medical stimulation device can route the electrical stimulation signals to the target site as well as allow the medical device to sense physiological signals occurring at the target site.

Certain types of stimulation therapy can be more effective by controlling the stimulation therapy based on how the body of the patient is responding to the stimulation therapy. For instance, in deep brain stimulation, it can be beneficial to sense for local field potentials between stimulation pulses and a stimulation signal characteristic such as the amplitude of the stimulation pulses may be adjusted based upon those local field potentials. Typically, a single mode threshold or a dual mode pair of thresholds are set for the patient, and the strength of the local field potential being sensed is compared to the single mode threshold or dual mode thresholds. In the single mode case, if the threshold is exceeded in the direction of interest, such as being stronger than a maximum threshold, then the stimulation characteristic may be altered in the way necessary to lower the local field potential, such as by increasing the stimulation amplitude. In the dual mode case with an upper and lower threshold, exceeding above the upper threshold or exceeding below the lower threshold calls for the stimulation characteristic such as amplitude to be altered in the way necessary to raise or lower the local field potential as needed.

While this approach to therapy can be beneficial, issues can arise. For instance, there can be local field potential drift toward and eventually beyond a threshold. In this case, the threshold may be continuously or nearly continuously exceeded which results in a continuous alteration to the stimulation characteristic in the same direction, i.e., lesser or greater amplitude, until the stimulation characteristic eventually reaches a stimulation limit where the stimulation adjustment can no longer occur in that direction. Thus, the stimulation control can no longer be responsive to fluctuation in the local field potential.

SUMMARY

Embodiments address issues such as these and others by adapting physiological signal thresholds used to control the stimulation therapy for a patient. For instance, the upper and/or lower threshold for a local field potential may be adapted by calculating one or more average values of the physiological signal over a period of time and then determining new upper and/or lower threshold values for the physiological signal to be subsequently used until a next update to the threshold(s). In this way, the threshold(s) can shift in value in response to the drifting of the physiological signal, which allows the stimulation characteristic such as amplitude to remain in the adjustable region between upper and lower stimulation characteristic limits established for the patient. Therefore, the stimulation characteristic can continue to be adjusted in a way that is responsive to the fluctuation in the physiological signal.

Embodiments provide a medical device that includes a sensing module that measures a physiological signal and a stimulation module that produces a stimulation signal having a stimulation characteristic. The medical device further includes a processing module that obtains a measurement of the physiological signal from the sensing module, computes a first average level of the physiological signal for a first time period, determines a first threshold based on the first average level of the physiological signal, and controls the stimulation module for a next time period by comparing the level of the physiological signal over a current time period immediately preceding the next time period to the first threshold and when the level of the physiological signal exceeds the first threshold during the current time period then adjusting the stimulation characteristic for the next time period in a direction that causes the physiological signal to no longer exceed the first threshold.

Embodiments provide a method of controlling stimulation therapy that involves measuring a physiological signal at a sensing module of the implantable medical device and producing a stimulation signal having a stimulation characteristic at a stimulation module of the implantable medical device. The method further involves obtaining a measurement of the physiological signal from the sensing module at a processing module and computing a first average level of the physiological signal for a first time period at the processing module. The method also involves determining a first threshold based on the first average level of the physiological signal at the processing module. Additionally, the method involves controlling the stimulation module for a next time period at the processing module by comparing the level of the physiological signal over a current time period immediately preceding the next time period to the first threshold and when the level of the physiological signal exceeds the first threshold during the current time period then adjusting the stimulation characteristic for the next time period to a level that causes the physiological signal to no longer exceed the first threshold.

DETAILED DESCRIPTION

Embodiments provide medical devices with the ability to adapt physiological signal threshold(s) when using such threshold(s) to adjust stimulation characteristics. This accounts for physiological signal drift where the physiological signal remains beyond an otherwise fixed threshold and thereby allows the stimulation characteristic to remain in the adjustable range, rather than becoming stuck at a limit established for the patient. By remaining in the adjustable range, the stimulation characteristic may continue to be adjusted as needed so as to be responsive to the physiological signal fluctuation to attempt to maintain the physiological signal within the threshold(s).

Figure 1:
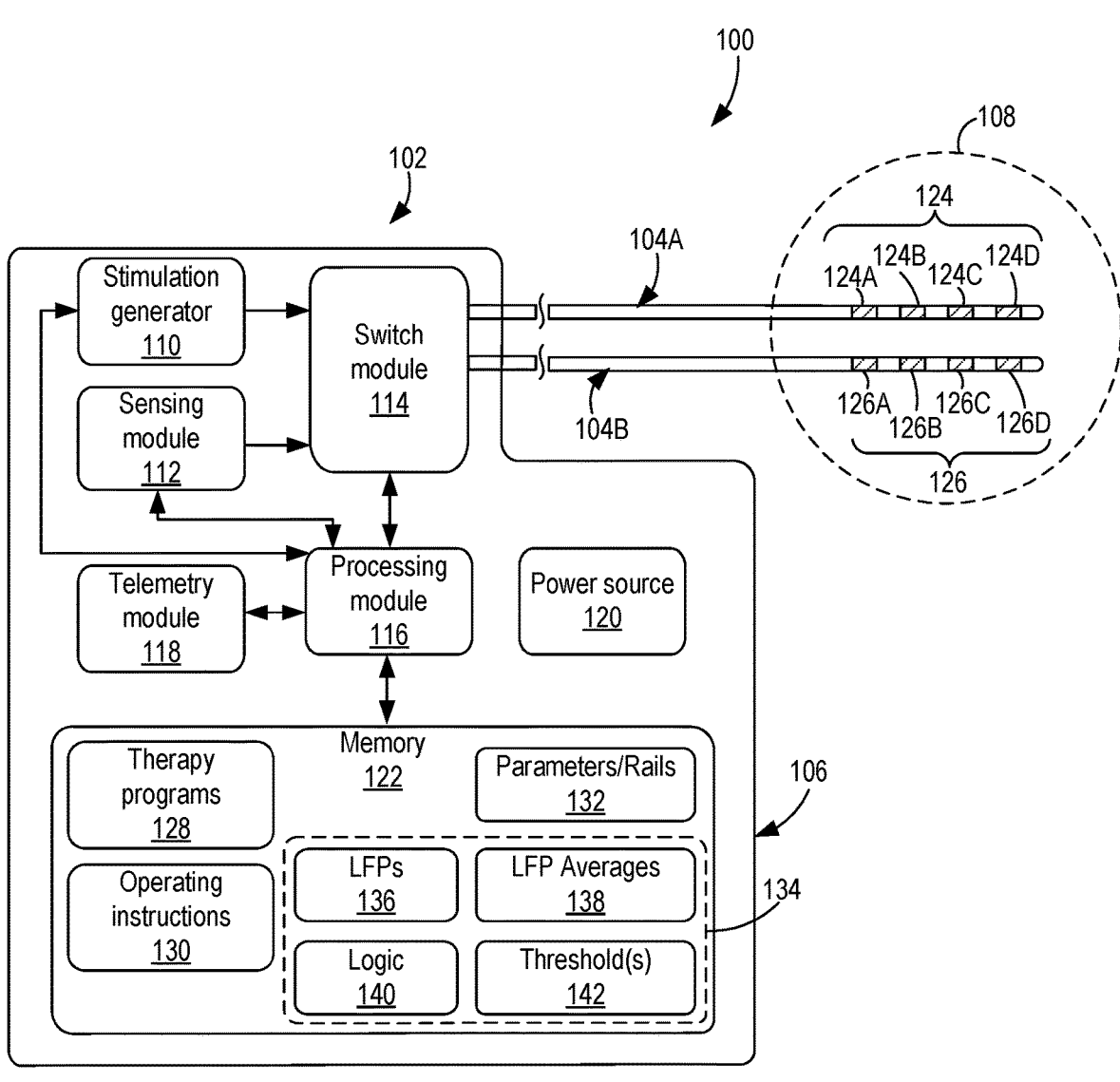
FIG. 1 shows an example of a medical system that controls stimulation therapy by adjusting physiological signal threshold(s).

FIG. 1 shows an example of a medical system 100 that includes a medical device 102 coupled to one or more medical leads 104A, 104B. The medical device may be external or implantable while the medical lead 104A, 104B is implantable and extends to a target region 108 within the body of the patient. For example, the target region 108 may be a particular location within the brain of the patient, and the medical system 100 provides deep brain stimulation via a collection of distal electrodes 124, 126 on the lead(s) 104A, 104B to address a neurological condition. While four distal electrodes 124A, 124B, 124C, 124D and 126A, 126B, 126C, and 126D are shown per lead 104A, 104B, it will be appreciated that a different number of electrodes may be present. Furthermore, it will be appreciated that a different number of leads may be present than those shown.

The medical device 102 includes several components within a housing 106. Where the medical device 102 is implantable, the housing 106 is constructed of a biocompatible material and is hermetically sealed to prevent ingress of bodily fluids into the interior where electrical circuitry is present. The electrical circuitry includes a power source 120 such as battery that provides power to the electrical components. The electrical circuitry includes a processing module 116 that may take the form of a general-purpose programmable processor, application specific processor, microcontroller, hard wired digital logic, and the like. The processing module 116 may perform various logical operations to cause additional modules to perform various functions. The processing module 116 utilizes either an integrated or otherwise separate but coupled memory 122.

The memory 122 may store various programming and data used by the processing module 116. The memory 122 may be of various forms and combinations thereof, including random access memory, read only memory, flash memory, and the like. The memory 122 may store operating instructions 130 that the processing module 116 implements to perform general operating functions including communicating with and instructing other modules to perform functions that provide the stimulation therapy.

The memory 122 may include therapy programming 128 that the processing module 116 may implement to instruct a stimulation generator 110 to produce electrical stimulation signals according to a set of therapy parameters 132 that may be programmed, including rails or limits for stimulation characteristics such as amplitude, pulse width, pulse interval, and the like. The therapy programming 128 may cause the processing module 116 to configure a switching module 114 to direct the output of the stimulation generator 110 to particular electrodes of the set 124, 126. The therapy programming 128 may also cause the programming module 116 to cause a sensing module 112 to sense physiological signals such as during a period of time between stimulation signal pulses where the processing module 116 configures the switching module 114 to connect particular electrodes of the set 124, 126 to the sensing module 112.

The memory 122 may also store a collection 134 of programming and data for the purpose of adapting the physiological signal thresholds used to adjust the stimulation characteristic. As described below with reference to FIG. 2, the processing module 116 may collect sample values of the physiological signal, such as the strength of local field potentials (LFPs) stored in a collection 136 and determine relevant averages of the physiological signal samples stored in a collection 138. The determination of the relevant averages may include performing operations such as those in the example of FIG. 2 according to logic 140. Additionally, the logic 140 may provide for additional operations such as those in the example of FIG. 4 to utilize the collection 138 of averages to determine a suitable set 142 of thresholds. The therapy program 128 may then implement those thresholds to adjust the stimulation amplitude accordingly as in the example shown in FIG. 7.

It will be appreciated that the therapy programs 128, operating instructions 130, parameters 132, and logic 140 may be programmable by virtue of communication with an external programming device. The processing module 116 may communicate with the external programming device via a telemetry module 118. The telemetry module 118 may provide for one of various types of communication, such as an inductive coupling, an arm's length coupling, a short-range radio frequency coupling such as in the Medical Implant Communications System (MICS) band, and the like.

Figure 2:
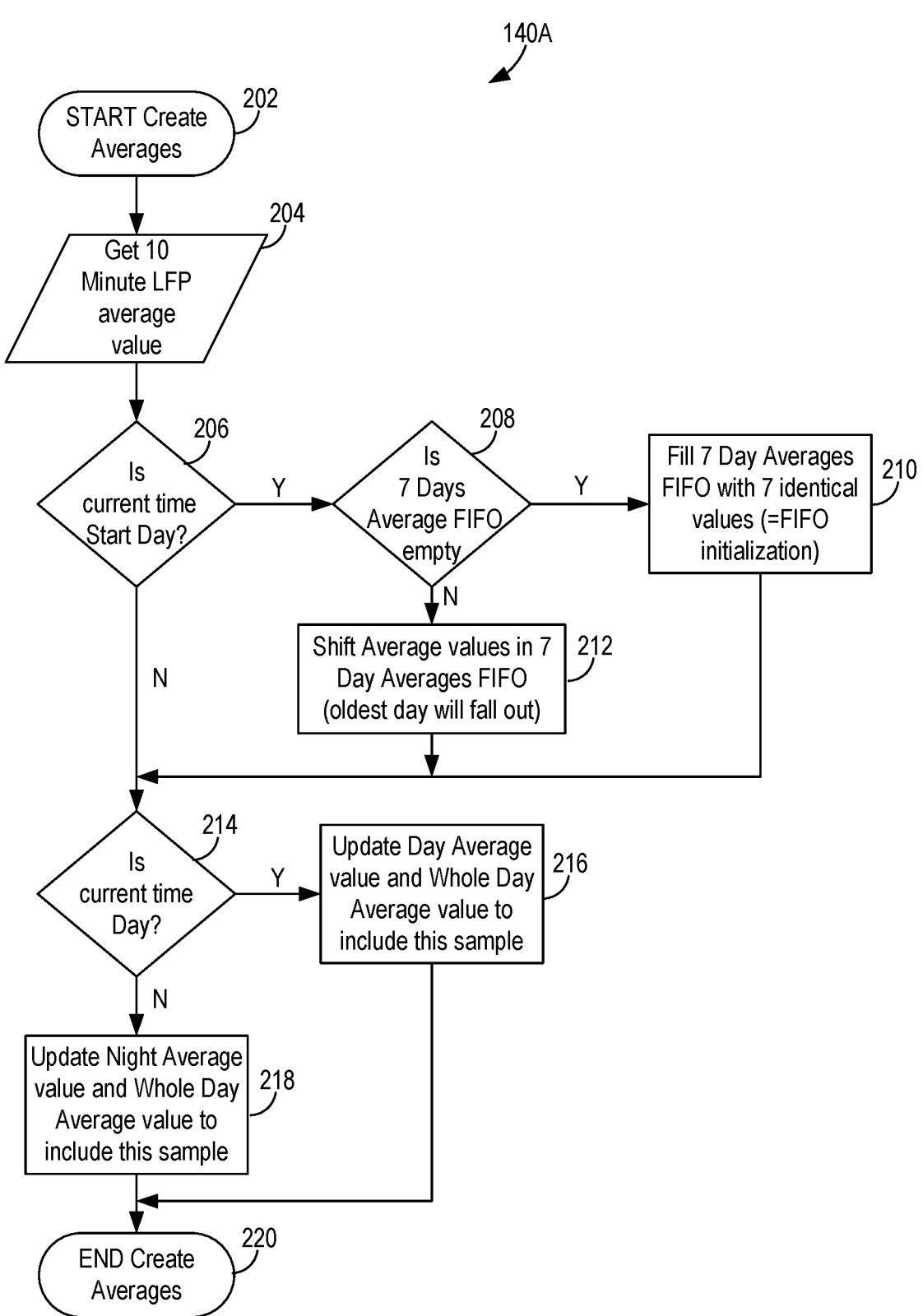
FIG. 2 shows an example of operations to find average values used when adjusting the physiological signal threshold(s).

In relation to FIG. 2, logical operations 140A are performed by the processing module 116 to create averages of the physiological signal value, such as LFP strength, for a desired time period. In this example, there are three separate averages being determined where the desired time period is a day. The three include a daytime average, a nighttime average, and a whole day average. However, to find these three separate averages for a day, an average value of the physiological signal may be obtained over smaller periods of time, such as for every 10 minutes. Thus, responsive to the operations beginning execution at initial stage 202, the processing module 116 receives physiological signal values over the smaller period of time, such as 10 minutes, and computes the average of those values at an operation 204.

Figure 3:
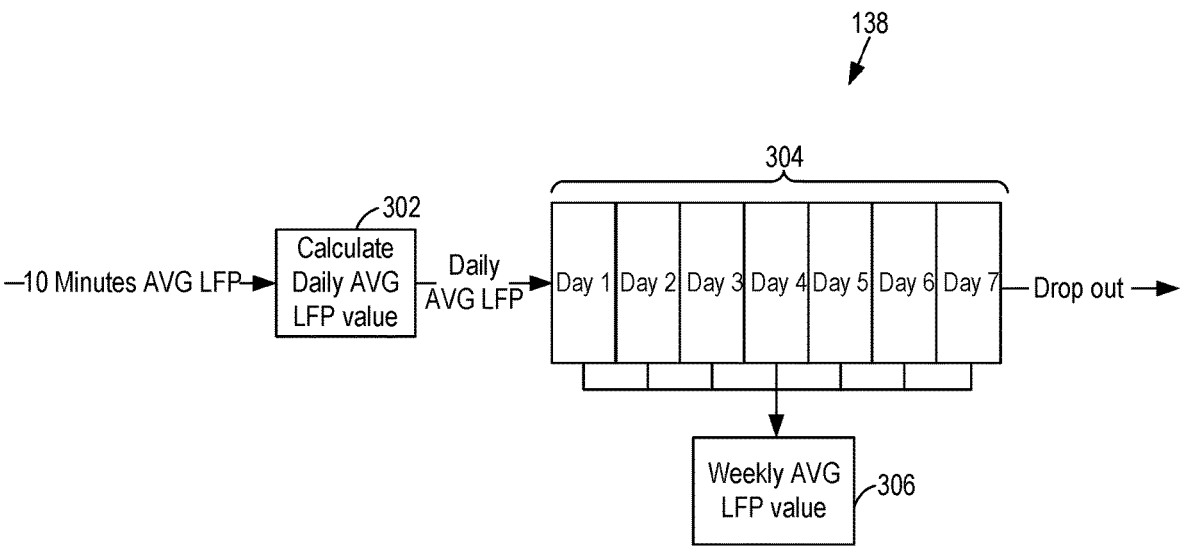
FIG. 3 shows an example of a progression of physiological signal averages used when adjusting the physiological signal threshold(s).

If the processing module 116 recognizes the current time as the start of a new day at operation 206 based on the internal clock of the processing module 116 or an external clock, the processing module 116 then determines whether a weekly average buffer is empty at an operation 208. FIG. 3 shows an example of this buffer 304. If the weekly average buffer is empty, then the processing module 116 fills the weekly average buffer with the latest calculated averages found at operation 216 and 218 to initialize the buffer in preparation for operating as a first in first out (FIFO) data store at operation 210. If the buffer is not empty at operation 208, then the processing module 116 shifts the average values in the buffer so that the oldest day falls out in preparation for obtaining the average for the current day at operation 212. This process then continues from either operation 210 or operation 212 to an operation 214. Likewise, if operation 206 finds that this is not the start of a new day, then the process continues directly to operation 214.

If the processing module 116 recognizes that the current time is daytime at the operation 214, then the processing module uses the current 10 minute average to update the daytime average and to update the whole day average at an operation 216. If the processing module 116 recognizes that the current time is nighttime at the operation 214, then the processing module uses the current 10 minute average to update the nighttime average and to update the whole day average at an operation 218. This iteration of the operations 140A then end at stage 220. However, after a 10 minute delay while physiological signal values are being collected, the processing module 116 may then perform the operations 140A again to further update the daytime, nighttime, and whole day averages being determined for the current day. This repeats throughout the day and then begins again for the next day and so on. Thus, this keeps the buffer 304 filled with the seven most recent days of the three averages for each of those seven days.

FIG. 3 shows the collection 138 of average values including the buffer 304. The three average values 302 of the most recent 10 minute span as calculated by the operations 140A of FIG. 2 are moved into the day 1 position of the buffer 304, the day 1 values are shifted to the day 2 values, and so on so that the day 7 values are shifted out. The processing module 116 may also calculate a weekly average 306 for each of the three average values (i.e., daytime, nighttime, and whole day) based on the current set of seven day values present in the buffer 304. This is further described with reference to FIG. 4.

Figure 4:
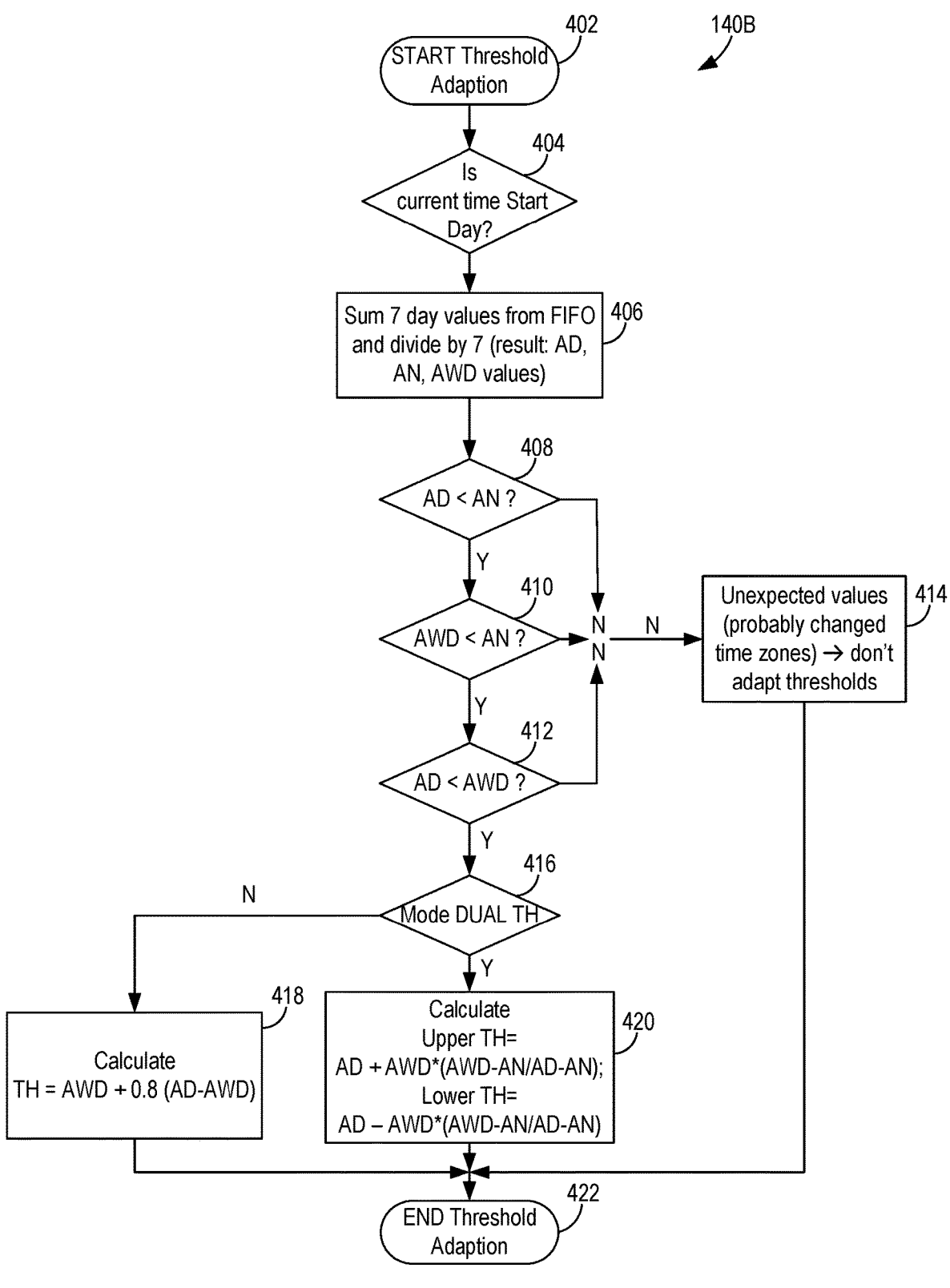
FIG. 4 shows an example of operations to determine the adjusted threshold(s) based on the average values.

In relation to FIG. 4, logical operations 140B are performed by the processing module 116 to find the current threshold values that should be used for analysis of the physiological signal. Thus, upon the operations beginning at initial stage 402, the processing module 116 determines if the current time is the start of a new day. In this example, the operations are such that thresholds are updated on a daily basis. Therefore, if operation 404 finds that this is the start of a new day, the operations continue. Otherwise, they wait until the new day is discovered. It will be appreciated that the thresholds may be updated on a different schedule than daily.

Once operation 404 finds the start of a new day, then processing module 116 finds the weekly average 306 of each of the three daily averages from the buffer 304 at an operation 406. Here, for each of the three daily averages (i.e., daytime, nighttime, and whole day), the processing module finds the weekly average of each by adding up all seven of the corresponding daily averages and dividing by seven. This produces the weekly average of daytime (AD), the average of nighttime (AN), and the average of the whole day (AWD).

Prior to using these three weekly average values, the processing module 116 may perform a test to ensure that the three values AD, AN, and AWD are legitimate. It is understood from knowledge of the natural function of the human body that the AD should be less than the AN as tested at operation 408, the AWD should be less than the AN as tested at operation 410, and the AD should be less than the AWD as tested at operation 412. If any of these tests fail, then the thresholds are maintained at their current values at operation 414 rather than being adapted with new values. For instance, the tests may fail because of a timing issue, such as where the time zones changed which caused daytime data to be considered nighttime data or the reverse. The process ends at stage 422 and then repeats after a delay period.

If the tests at operations 408, 410, and 412 pass, then the processing module 116 may consider whether the current mode of therapy utilizes a dual threshold mode or a single threshold mode at an operation 416. If single threshold mode is being used, then the processing module computes the single threshold at an operation 418. One example of the calculation is shown for operation 418 but it will be appreciated that other manners of calculating the single threshold are also possible. In this particular example, the single threshold is based on only the daytime average (AD) and the whole day average (AWD). If dual threshold mode is being used, then the processing module computes the upper and lower thresholds at an operation 420. One example of the calculation is shown for operation 420 but it will be appreciated that other manners of calculating the upper and lower thresholds are also possible. In this particular example, both the upper and lower thresholds are based on the daytime average (AD), the nighttime average (AN), and the whole day average (AWD). The process ends at stage 422 and then repeats after a delay period.

Figure 5:
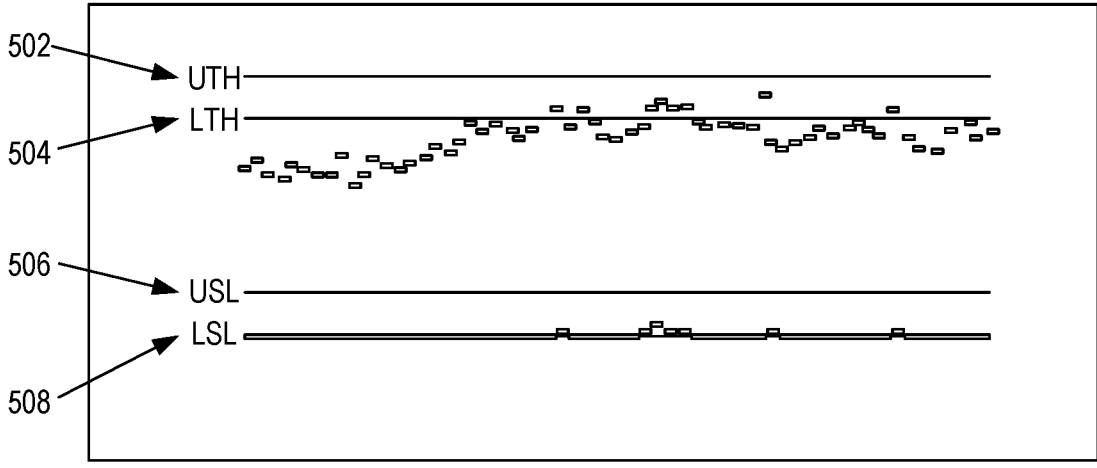
FIG. 5 shows an example of physiological signal samples and fixed threshold(s) where the samples have drifted beyond the threshold causing stimulation amplitude to stay at or near the limit established for the patient and no longer be adequately adjustable to be responsive to the change in the physiological signal.

FIG. 5 shows an example of physiological signal values measured over a period of time relative to a fixed upper threshold (UTH) 502 and a fixed lower threshold (LTH) 504 FIG. 5 further shows the stimulation characteristic, in this case stimulation amplitude, between an upper stimulation limit (USL) 506 and a lower stimulation limit (LSL) 508. It can be seen that the physiological signal values have drifted to exceed the lower threshold 504 by going below the lower threshold 504 for the majority of the samples shown. As a result, the therapy program attempts to raise the physiological signal values by dropping the stimulation amplitude. However, as shown, the stimulation amplitude has reached the lower stimulation limit 508 and cannot go low enough to effectively raise the value of the physiological signals. Thus, the therapy is less effective than desired.

Figure 6:
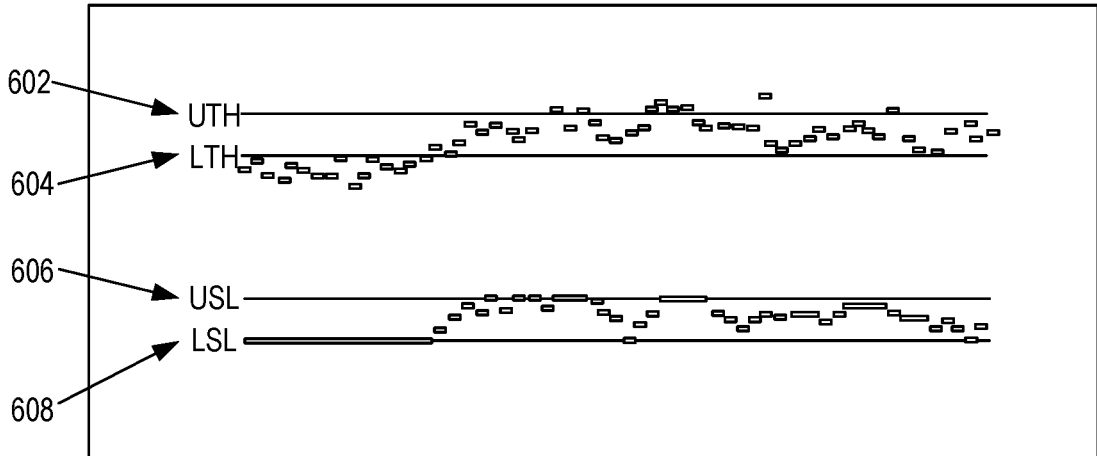
FIG. 6 shows an example of physiological signal samples and adapted thresholds allowing the stimulation amplitude to be adjusted to be responsive to the fluctuations in the physiological signal.

FIG. 6 shows an example of the same physiological signal values shown in FIG. 6, but with adapted upper threshold 602 and lower threshold 604. Because of the adaptation, it can be seen that the lowest physiological signal values are now close to the lower threshold. Thus, the stimulation amplitude being at that lower stimulation limit 608 raises the physiological signal values above the lower threshold 604 and even to the upper threshold 602. The stimulation amplitude can then be adjusted toward the upper stimulation limit 606 to bring the physiological signal values back toward the lower threshold 604. Thus, the fluctuation of the physiological signal between the upper and lower thresholds as preserved by adjusting the stimulation waveform accordingly, producing a more beneficial stimulation therapy.

Figure 7:
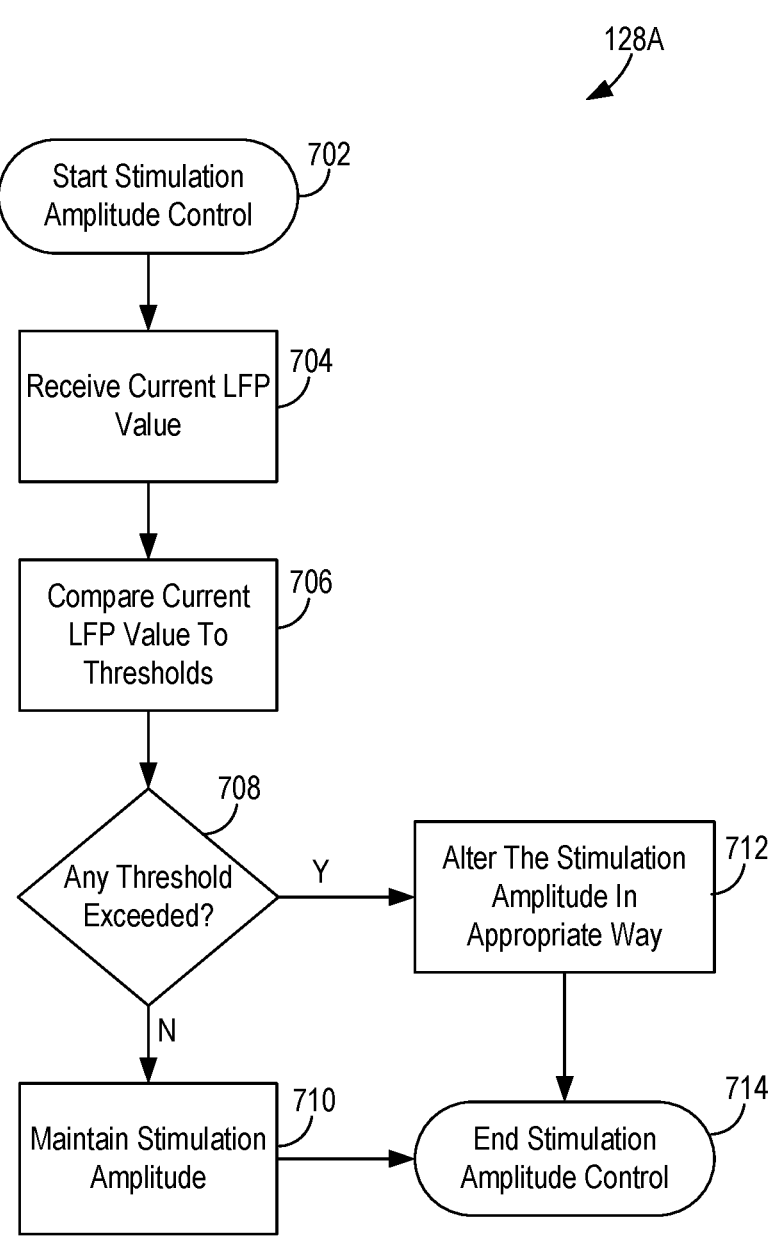
FIG. 7 shows an example of operations to implement the adapted thresholds to adjust the stimulation amplitude to be responsive to the fluctuations of the physiological signal and attempt to cause the physiological signal to no longer exceed the threshold(s).

FIG. 7 shows an example of operations 128A that may be performed to utilize the adjusted thresholds from the operations 140B of FIG. 4 in order to produce a result like that shown in FIG. 6. At an initial stage 702, the stimulation control, in this example stimulation amplitude control, begins. The processing module 116 receives the current physiological signal value, such as an LFP value, at an operation 704. The processing module 116 compares the current physiological signal value of a current time period to the threshold(s) at an operation 706. The processing module 116 detects whether the physiological value is exceeding a threshold at an operation 708. As an alternative to detecting if the physiological signal is exceeding the threshold, the processing module 116 may determine if the physiological signal value is within a given amount from the threshold. In either case, the processing module 116 is determining whether it is worthwhile to adjust the stimulation characteristic to compensate in the next timer period that the current time period immediately precedes.

If compensation is not necessary, then the processing module maintains the stimulation characteristic at operation 710 for the next time period. If compensation is necessary, then the processing module adjusts the stimulation characteristic at operation 712 for the next time period. The stimulation amplitude control iteration ends at stage 714 and then repeats for the next available physiological signal value.

As can be seen from the discussion above, adapting thresholds for drifting physiological signal values allows stimulation adjustments to be made to compensate and cause a physiological signal value that has approached or exceeded an adjusted threshold to then no longer exceed or continue approaching the threshold. By continuing to collect average values as in FIG. 2 and computer thresholds as in FIG. 4, the ongoing therapy made more beneficial by the ongoing adjustment to the stimulation characteristic that provides the desired influence on the physiological signal.

While embodiments have been particularly shown and described, it will be understood by those skilled in the art that various other changes in the form and details may be made therein without departing from the spirit and scope of the invention.

What is claimed is:

1. A medical device, the medical device comprising:
   a stimulation generator configured to produce a stimulation signal having a stimulation characteristic; and
   processing circuitry configured to:
      control the stimulation generator to deliver the stimulation signal based on a first threshold;
      obtain a measurement of a physiological signal sensed via electrodes,
      compute a first average level of the physiological signal for a first time period,
      adjust the first threshold to a second threshold based on the first average level of the physiological signal, and
      control the stimulation generator for a next time period by comparing the level of the physiological signal over a current time period immediately preceding the next time period to the second threshold;
      wherein to control the stimulation generator for the next time period, the processing circuitry is configured to, in response to the level of the physiological signal exceeding the second threshold during the current time period, adjust the stimulation characteristic of the stimulation signal for the next time period to a level that causes the physiological signal to no longer exceed the second threshold, wherein the physiological signal comprises local field potentials (LFPs) within neurological tissue and the stimulation characteristic is stimulation amplitude.

2. The medical device of claim 1, wherein the second threshold is a second upper threshold, wherein the processing circuitry further determines a second lower threshold based on the first average level of the physiological signal, and further controls the stimulation generator for the next time period by at least:

comparing the level of the physiological signal over the current time period immediately preceding the next time period to the second lower threshold; and in response to the physiological signal being below the second lower threshold continuously during the current time period, adjusting the stimulation characteristic for the next time period to a level that causes the physiological signal to no longer be below the second lower threshold.

3. The medical device of claim 1, wherein the first average level of the physiological signal is an all day average level, and wherein the processing circuitry is further configured to compute a daytime average level of the physiological signal for the first time period and determine the first threshold based on the all day average level and the daytime average level.

4. The medical device of claim 3, wherein the processing circuitry is further configured to compute a nighttime average level of the physiological signal for the first time period and determine the first threshold based on the all day average level, the daytime average level, and the nighttime average level.

5. The medical device of claim 4, wherein the processing circuitry is further configured to determine the second threshold based on the all day average level, the daytime average level, and the nighttime average level, and control the stimulation generator for the next time period by at least comparing the level of the physiological signal over the current time period immediately preceding the next time period to the second threshold, and, in response to the physiological signal exceeding the second threshold continuously during the current time period, adjust the stimulation amplitude for the next time period to a level that causes the physiological signal to no longer exceed the second threshold.

6. The medical device of claim 1, wherein the first time period is a week.

7. The medical device of claim 1, wherein the processing circuitry is configured to obtain an average sample level of the measurements taken over a 10 minute span during the first time period, and wherein the processing circuitry is configured to compute the first average level from a collection of the average sample levels obtained during the first time period.

8. The medical device of claim 7, wherein the first time period is represented by a first in first out buffer and the processing circuitry is configured to continuously obtain the average sample levels at the 10 minute intervals to maintain the collection of the average sample levels within the first in first out buffer.

9. The medical device of claim 8, wherein the processing circuitry is configured to continuously compute the first average level at the 10 minute intervals and compute the first threshold on a daily basis.

10. The medical device of claim 1, wherein the first threshold is a first lower threshold and the second threshold is a second lower threshold, and wherein the processing circuitry is configured to:
   control the stimulation generator to deliver the stimulation signal based on the first lower threshold and a first upper threshold;
   adjust, based on the first average level of the physiological signal, the first upper threshold to a second upper threshold;
   control the stimulation generator for the next time period by comparing the level of the physiological signal over the current time period immediately preceding the next time period to the second upper threshold; and in response to the level of the physiological signal exceeding the second upper threshold during the current time period, adjusting the stimulation characteristic of the stimulation signal for the next time period to the level that causes the physiological signal to no longer exceed the second upper threshold.

11. A method of controlling stimulation therapy, the method comprising:

producing a stimulation signal having a stimulation characteristic at a stimulation generator of the implantable medical device;

controlling, by processing circuitry, the stimulation generator to deliver the stimulation signal based on a first threshold;

obtaining, by the processing circuitry, a measurement of a physiological signal sensed via electrodes;

computing, by the processing circuitry, a first average level of the physiological signal for a first time period;

adjusting, by the processing circuitry, a first threshold to a second threshold based on the first average level of the physiological signal; and controlling, by the processing circuitry, the stimulation generator for a next time period by comparing the level of the physiological signal over a current time period immediately preceding the next time period to the second threshold;

wherein controlling the stimulation generator for the next period comprises, in response to the level of the physiological signal exceeding the second threshold during the current time period, adjusting, by the processing circuitry, the stimulation characteristic of the stimulation signal for the next time period to a level that causes the physiological signal to no longer exceed the second threshold, wherein the physiological signal comprises local field potentials (LFPs) within neurological tissue and the stimulation characteristic is amplitude.

12. The method of claim 11, wherein the second threshold is a second upper threshold, and wherein the method further comprises:

determining a second lower threshold based on the first average level of the physiological signal; and controlling the stimulation generator for a next time period by:

comparing the level of the physiological signal over the current time period immediately preceding the next time period to the second lower threshold; and responsive to the physiological signal being below the second lower threshold continuously during the current time period, adjusting the stimulation characteristic for the next time period to a level that causes the physiological signal to no longer be below the second lower threshold.

13. The method of claim 11, wherein the first average level of the physiological signal is an all day average level, and wherein the method further comprises computing, by the processing circuitry, a daytime average level of the physiological signal for the first time period and determining, by the processing circuitry, the first threshold based on the all day average level and the daytime average level.

14. The method of claim 13, further comprising computing, by the processing circuitry, a nighttime average level of the physiological signal for the first time period and determining, by the processing circuitry, the first threshold based on the all day average level, the daytime average level, and the nighttime average level.

15. The method of claim 11, further comprising:

determining, by the processing circuitry, the second threshold based on the all day average level, the daytime average level, and the nighttime average level; and controlling, by the processing circuitry, the stimulation module for a next time period by comparing the level of the physiological signal over the current time period immediately preceding the next time period to the second threshold and, responsive to the physiological signal exceeding the second threshold continuously during the current time period, adjusting the stimulation characteristic for the next time period to a level that causes the physiological signal to no longer exceed the second threshold.

16. The method of claim 11, wherein the first time period is a week.

17. The method of claim 11, further comprising obtaining, by the processing circuitry, an average sample level of the measurements taken over a 10 minute span during the first time period and computing, by the processing circuitry, the first average level from a collection of the average sample levels obtained during the first time period.

18. The method of claim 17, wherein the first time period is represented by a first in first out buffer, and wherein the method further comprises continuously obtaining the average sample levels at the 10 minute intervals to maintain the collection of the average sample levels within the first in first out buffer.

19. A medical device comprising:

a stimulation generator configured to produce a stimulation signal having a stimulation characteristic; and processing circuitry configured to:

control the stimulation generator to deliver the stimulation signal based on a first threshold;

obtain a measurement of a physiological signal sensed via electrodes, compute an all day average level of the physiological signal for a first time period, compute a daytime average level of the physiological signal for the first time period; and adjust the first threshold to a second threshold based on the all day average level of the physiological signal and the daytime average level of the physiological signal, control the stimulation generator for a next time period by comparing the level of the physiological signal over a current time period immediately preceding the next time period to the second threshold, wherein to control the stimulation generator for the next time period, the processing circuitry is configured to, in response to the level of the physiological signal exceeding the second threshold during the current time period, adjust the stimulation characteristic of the stimulation signal for the next time period to a level that causes the physiological signal to no longer exceed the second threshold.

20. The medical device of claim 19, wherein the processing circuitry is further configured to:

compute a nighttime average level of the physiological signal for the first time period; and determine the first threshold based on the all day average level, the daytime average level, and the nighttime average level.

* * * * *